(12) United States Patent
Loozen et al.

(10) Patent No.: US 7,838,516 B2
(45) Date of Patent: Nov. 23, 2010

(54) 15 β-SUBSTITUTED STEROIDS HAVING SELECTIVE ESTROGENIC ACTIVITY

(75) Inventors: Hubert Jan Jozef Loozen, Oss (NL); Antonius Gerardus Hendrikus Ederveen, Oss (NL); Fredericus Antonius Dijcks, Oss (NL)

(73) Assignee: N.V. Organon, Oss (NL)

( * ) Notice: Subject to any disclaimer, the term of this patent is extended or adjusted under 35 U.S.C. 154(b) by 361 days.

(21) Appl. No.: 11/662,166

(22) PCT Filed: Sep. 5, 2005

(86) PCT No.: PCT/EP2005/054368

§ 371 (c)(1),
(2), (4) Date: Apr. 23, 2007

(87) PCT Pub. No.: WO2006/027347

PCT Pub. Date: Mar. 16, 2006

(65) Prior Publication Data

US 2007/0254860 A1    Nov. 1, 2007

Related U.S. Application Data

(60) Provisional application No. 60/608,501, filed on Sep. 8, 2004.

(30) Foreign Application Priority Data

Sep. 8, 2004 (EP) .................................. 04104334

(51) Int. Cl.
*A61K 31/565* (2006.01)
*C07J 1/00* (2006.01)
(52) U.S. Cl. ..................... 514/182; 552/629
(58) Field of Classification Search .................. 552/629; 514/182
See application file for complete search history.

(56) References Cited

U.S. PATENT DOCUMENTS

| | | | |
|---|---|---|---|
| 3,007,946 A | 11/1961 | Tyner | |
| 3,049,555 A | 8/1962 | Tyner | |
| 3,092,645 A | 6/1963 | Nicholson | |
| 3,257,429 A * | 6/1966 | Ringold et al. | 552/528 |
| 3,299,108 A | 1/1967 | Baran | |
| 3,377,366 A | 4/1968 | Baran | |
| 3,464,979 A | 9/1969 | Barton | |
| 3,465,010 A | 9/1969 | Baran | |
| 3,642,992 A * | 2/1972 | Babcock et al. | 514/170 |
| 3,652,606 A | 3/1972 | Baran | |
| 3,704,253 A | 11/1972 | Reinhardt et al. | |
| 3,766,224 A * | 10/1973 | Coombs | 552/629 |
| 4,272,530 A | 6/1981 | Teutsch et al. | |
| 5,116,830 A | 5/1992 | Tanabe et al. | |
| 5,686,437 A | 11/1997 | Labrie et al. | |
| 6,541,465 B2 | 4/2003 | Loozen et al. | |
| 6,677,329 B1 | 1/2004 | Loozen et al. | |
| 6,780,854 B2 | 8/2004 | Loozen et al. | |
| 6,989,378 B2 | 1/2006 | Leysen et al. | |
| 2005/0153949 A1 | 7/2005 | Leysen et al. | |

FOREIGN PATENT DOCUMENTS

| | | |
|---|---|---|
| DE | 1084261 | 6/1960 |
| DE | 2757157 | 6/1979 |
| EP | 0 145 493 | 3/1989 |
| EP | 0 613 687 | 9/1994 |
| EP | 0 798 378 | 10/1997 |
| EP | 0869132 A1 | 10/1998 |
| GB | 0 890 989 | 3/1962 |
| GB | 1 341 601 A | 12/1973 |
| WO | WO 94/18224 | 8/1994 |
| WO | WO 99/45886 | 9/1999 |
| WO | WO 00/31112 | 6/2000 |

OTHER PUBLICATIONS

International Search Report, dated Jan. 23, 2006, for International Application No. PCT/EP2005/054368.
An English language abstract and a machine translation of DE1084261, 1960.
Two English language abstracts of DE2757157, 1979.
Avery et al., "Synthesis and Testing of 17αβ-hydroxy-7α-methyl-D-homoestra-4,16-dien-3-one: A Highly Potent Orally Action Androgen," Steroids 55 (1990) 59-64.
Baggett et al., "Effects of Two Metabolites of Norethynodrel on Reproductive Performance of Female Rats," *Fertility And Sterility* 21, (1970) 68-72.
Becker et al. (eds) *Behavior Endocrinology* (1992) 82-84.

(Continued)

*Primary Examiner*—Barbara P Badio
(74) *Attorney, Agent, or Firm*—Susan L. Hess

(57) ABSTRACT

The invention provides 15β-substituted steroidal compounds having selective estrogen receptor activity according to Formula I:

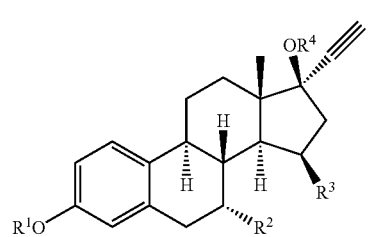

wherein,
$R^1$ is H, $C_{1-5}$ alkyl, $C_{1-12}$ acyl, di-($C_{1-5}$ alkyl)aminocarbonyl, ($C_{1-5}$alkyl)oxycarbonyl or sulfamoyl,
$R^2$ is H, $C_{1-3}$ alkyl, $C_{2-3}$ alkenyl or $C_{2-3}$ alkynyl, each of which may be optionally substituted with a halogen,
$R^3$ is $C_{1-2}$ alkyl, ethenyl or ethynyl, each of which may be optionally substituted with a halogen, and
$R^4$ is H or $C_{1-12}$ acyl.

13 Claims, No Drawings

OTHER PUBLICATIONS

De Gooyer et. al., "Receptor profiling and endocrine interactions of tibolone," Steroids 68 (2003) 21-30.

Fevig et al., "Estrogen Receptor Binding Tolerance of 16-Alpha-Substituted Estradiol Derivatives," *Steroids* 51(1988) 471-498.

González et. al., "Synthesis and Pharmacological Evaluation of 8α-Estradiol Derivatives," *Steroids* 40 (1982) 171-187.

Mosselman et. al., "Erβ: identification and characterization of a novel human estrogen Receptor," *FEBS Letters* 392 (1996) 49-53.

Solo et al., "7α-Alkyltestosterone Derivatives: Synthesis and Activity as Androgens and as Aromatase Inhibitors," Steroids 40 (1982) 603-614.

Takikawa, H., "The Competitive action of 16β-Ethylestradiol on the Binding of Estrogen Receptor in Human Breast Cancer," *Res. Steroids* 7 (1977) 291-299.

Tedesco et al., "7α,11β-disubstituted estrogens: probes for the shape of the ligand binding pocket in the estrogen receptor," *Bioorganic & Medicinal Chemistry Letters* 7 (1997) 2919-2924.

Writing Group for the Women's Health Initiative Investigators, "Risks and benefits of estrogen plus progestin in healthy postmenopausal women: principal results from The Women's Health Initiative randomized controlled trial," *JAMA* 288 (2002) 321-333.

\* cited by examiner

15 β-SUBSTITUTED STEROIDS HAVING SELECTIVE ESTROGENIC ACTIVITY

The present invention relates to a 15β-substituted steroidal compound having selective estrogenic activity, a pharmaceutical composition comprising said compound, said compound for use in therapy, and to the use of said compound for the manufacture of a medicament for the treatment or prevention of estrogen receptor-related diseases or regulation or treatment or prevention of other estrogen receptor-related physiological conditions.

Compounds with affinity for estrogen receptors have, for many years, found widespread use for the treatment of a range of medical conditions. Since the tissue distribution of estrogen receptors is broad, the therapeutic utility of estrogen receptor ligands is significant. In particular, their use has been implicated in contraception and the prevention or treatment of:

climacteric complaints: hot flushes, sweating and mood swings;

bone loss due to: osteoporosis, osteoarthritis, hypocalcemia, hypercalcemia, Paget's disease, osteomalacia, osteohalisteresis, multiple myeloma;

bone fractures;

urinary incontinence, urogenital atrophy, vaginal and skin atrophy, acne, melanoma, hirsutism;

benign breast disease, breast cancer, gynecomastia; and cardiovascular disease, high cholesterol levels, high LDL levels, coagulation disease, restenosis, vascular smooth muscle cell proliferation.

Despite the long availability, however, of compounds, particularly steroids, which can be used to provide relief for such estrogen receptor-related conditions, there still remains a need for new economic, effective and safe drug treatments.

Compounds having estrogenic activity are presently used in women as a medicament for the treatment of per- and/or post-menopausal (climacteric) complaints and osteoporosis. For women with an intact uterus, however, these non-selective estrogens, e.g. conjugated equine estrogens, 17β-estradiol, and 17α-ethynyl-17β-estradiol, cannot be prescribed for long-term therapy (>3 months) since these compounds induce a high degree of endometrial proliferation (follicular phase-like changes) leading to bleeding, endometrial hyperplasia and/or endometrial cancer. General clinical practice is to combine these non-selective estrogens with a progestagenic compound, a procedure that is well-known to reduce the endometrial stimulation and shift the endometrium from a follicular phase-like to luteal phase-like and/or atrophic endometrium. Unfortunately, the addition of a progestagenic compound to this treatment increases the risk for breast cancer as was demonstrated in the recent Women's Health Initiative (WHI) studies (see Writing Group for the Women's Health Initiative Investigators. Risks and benefits of estrogen plus progestin in healthy postmenopausal women: principal results from The Women's Health Initiative randomized controlled trial. JAMA 2002; 288:321-333).

Following the discovery of two distinct subtypes of estrogen receptors, denoted as ERα and ERβ, there now exists the possibility to discover subtype-selective estrogen receptor ligands. Since the two subtypes have different distribution in human tissues, such subtype-selective compounds may provide effective treatment or prevention of estrogen receptor-related conditions with minimal side-effects.

It has now been found that a series of 15β-substituted estradiol derivatives are potent steroids which possess good levels of functional selectivity for the estrogen receptor α-subtype. The present invention provides compounds of Formula I:

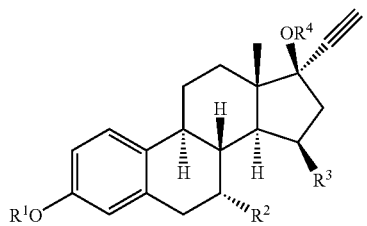

wherein, $R^1$ is H, $C_{1-5}$ alkyl, $C_{1-12}$ acyl, di-($C_{1-5}$ alkyl)aminocarbonyl, ($C_{1-5}$ alkyl)oxycarbonyl or sulfamoyl, $R^2$ is H, $C_{1-3}$ alkyl, $C_{2-3}$ alkenyl or $C_{2-3}$ alkynyl, each of which may be optionally substituted with a halogen, $R^3$ is $C_{1-2}$ alkyl, ethenyl or ethynyl, each of which may be optionally substituted with a halogen, and $R^4$ is H or $C_{1-12}$ acyl.

The steroids wherein $R^1$ and/or $R^4$ are/is not hydrogen are so-called prodrugs.

The term $C_{1-5}$alkyl, as used in the definition of Formula I, represents a branched or unbranched alkyl group having 1-5 carbon atoms. Examples of such groups are methyl, ethyl, isopropyl, tertiary butyl and pentyl. Similarly, the term $C_{1-3}$ alkyl and $C_{1-2}$ alkyl mean a(n) (branched or unbranched) alkyl group having 1-3 and 1-2 carbon atoms, respectively.

The term $C_{2-3}$ alkenyl represents a branched or unbranched alkenyl group having 2-3 carbon atoms and one double bond. Examples of such groups include ethenyl and propen-2-yl.

The term $C_{2-3}$ alkynyl represents an alkynyl group having 2-3 carbon atoms and one triple bond. Examples of such groups include ethynyl and propynyl.

The term $C_{1-12}$ acyl represents an acyl group derived from a carboxylic acid having 1-12 carbon atoms. The acyl group can comprise a hydrocarbon which may be branched, unbranched, saturated or unsaturated. Examples of such groups include formyl, acetyl, propanoyl, propenoyl, pivaloyl, heptanoyl, decanoyl, and undecanoyl. Also included within the definition of $C_{1-12}$ acyl are groups derived from dicarboxylic acids like hemi-maloyl, hemi-succinoyl and hemi-glutaroyl.

An example of a di-($C_{1-5}$ alkyl)aminocarbonyl group is dimethylcarbamoyl. An example of a ($C_{1-5}$ alkyl)oxycarbonyl group is ethoxycarbonyl.

A halogen may be one or more halogen atoms, such as one or more chlorine or fluorine atoms.

In one embodiment of the present invention, $R^2$ is $C_{1-3}$ alkyl, $C_{2-3}$ alkenyl or $C_{2-3}$ alkynyl, each of which may be optionally substituted with a halogen.

In another embodiment, $R^1$ and $R^4$ are both H.

In another embodiment, $R^1$ is H, $R^2$ is H, $C_{1-3}$ alkyl, $C_{2-3}$ alkenyl or $C_{2-3}$ alkynyl, $R^3$ is $C_{1-2}$ alkyl, ethenyl or ethynyl, and $R^4$ is H.

In another embodiment, $R^1$ is H $R^2$ is H or $C_{1-3}$ alkyl optionally substituted with a halogen, $R^3$ is $C_{1-2}$ alkyl optionally substituted with a halogen, and $R^4$ is H.

In another embodiment, $R^1$ is H, $R^2$ is H or $C_{1-3}$ alkyl, $R^3$ is $C_{1-2}$alkyl, and $R^4$ is H.

In another embodiment, $R^1$ is H, $R^2$ is H or $C_{1-2}$ alkyl, $R^3$ is methyl, and $R^4$ is H.

In another embodiment the compound is 7α-ethyl-15β-methyl-19-nor-17α-pregna-1,3,5(10)-trien-20-yne-3, 17β-diol.

In another embodiment, $R^1$ is H, $C_{1-5}$ alkyl or $C_{1-12}$ acyl, $R^2$ is H or $C_{1-3}$ alkyl, $R^3$ is $C_{1-2}$ alkyl, and $R^4$ is H or $C_{1-12}$ acyl.

In another embodiment, $R^1$ is H, $C_{1-5}$ alkyl or $C_{1-12}$ acyl, $R^2$ is $C_{1-3}$ alkyl, $R^3$ is methyl, and $R^4$ is H or $C_{1-12}$ acyl.

In another embodiment, $R^1$ is H, $C_{1-5}$ alkyl or $C_{1-12}$ acyl, $R^2$ is ethyl, $R^3$ is methyl, and $R^4$ is H or $C_{1-12}$ acyl.

In another embodiment, $R^1$ is H or $C_{1-12}$ acyl, $R^2$ is H or $C_{1-3}$ alkyl, $R^3$ is $C_{1-2}$ alkyl, and $R^4$ is H or $C_{1-12}$ acyl.

In another embodiment, $R^1$ is H or $C_{1-12}$ acyl, $R^2$ is H or $C_{1-3}$ alkyl, $R^3$ is methyl, and $R^4$ is H or $C_{1-12}$ acyl.

In another embodiment, $R^1$ is H or $C_{1-12}$ acyl, $R^2$ is ethyl, $R^3$ is methyl, and $R^4$ is H or $C_{1-12}$ acyl.

The compounds of the present invention can be synthesised according to methods well known in the art of organic chemistry in general and especially in the art of steroid chemistry. See, for example, Fried, J. and Edwards, J. A., '*Organic Reactions in Steroid Chemistry*,' Volumes I and II, van Nostrand Reinhold Company, New York, 1972; and C. Djerassi, '*Steroid Reactions*,' Holden-Day, Inc., San Francisco, 1963. The general synthetic procedure used to prepare the compounds described in the examples below is depicted in Scheme I. Variations to this scheme can easily be made by one skilled in the art.

Substrate A, the starting material for the synthetic procedure shown in Scheme I is synthesised in 4 steps. Firstly, conjugate additions of organometallic species (e.g., cuprates) to C17-protected estra-4,6-dien-3-ones provide the required 7α-substituted estr-4-en-3-ones. Minor amounts of 7β-isomers formed can be readily removed either by chromatography or crystallisation at this stage of the synthesis, or occasionally at later stages. The 7α-substituted estrenones are aromatised readily by using e.g., halogenation/dehalogenation procedures, to 7α-estrones, which upon alkylation at C3 and deprotection at C17 provide substrate A.

The α,β-unsaturated ketone C is obtained upon oxidation of the silyl enol ether B using, e.g., palladium diacetate. Michael addition to C using an organometallic species, e.g., a dialkyl cuprate then provides the adduct D. The methyl estrone D upon deprotection using, e.g., boron trifluoride dimethylsulphide complex then provides the phenol E, which is reprotected as, e.g., the silyl ether F. Addition of e.g., lithium acetylide to the ketone F to give the adduct G followed

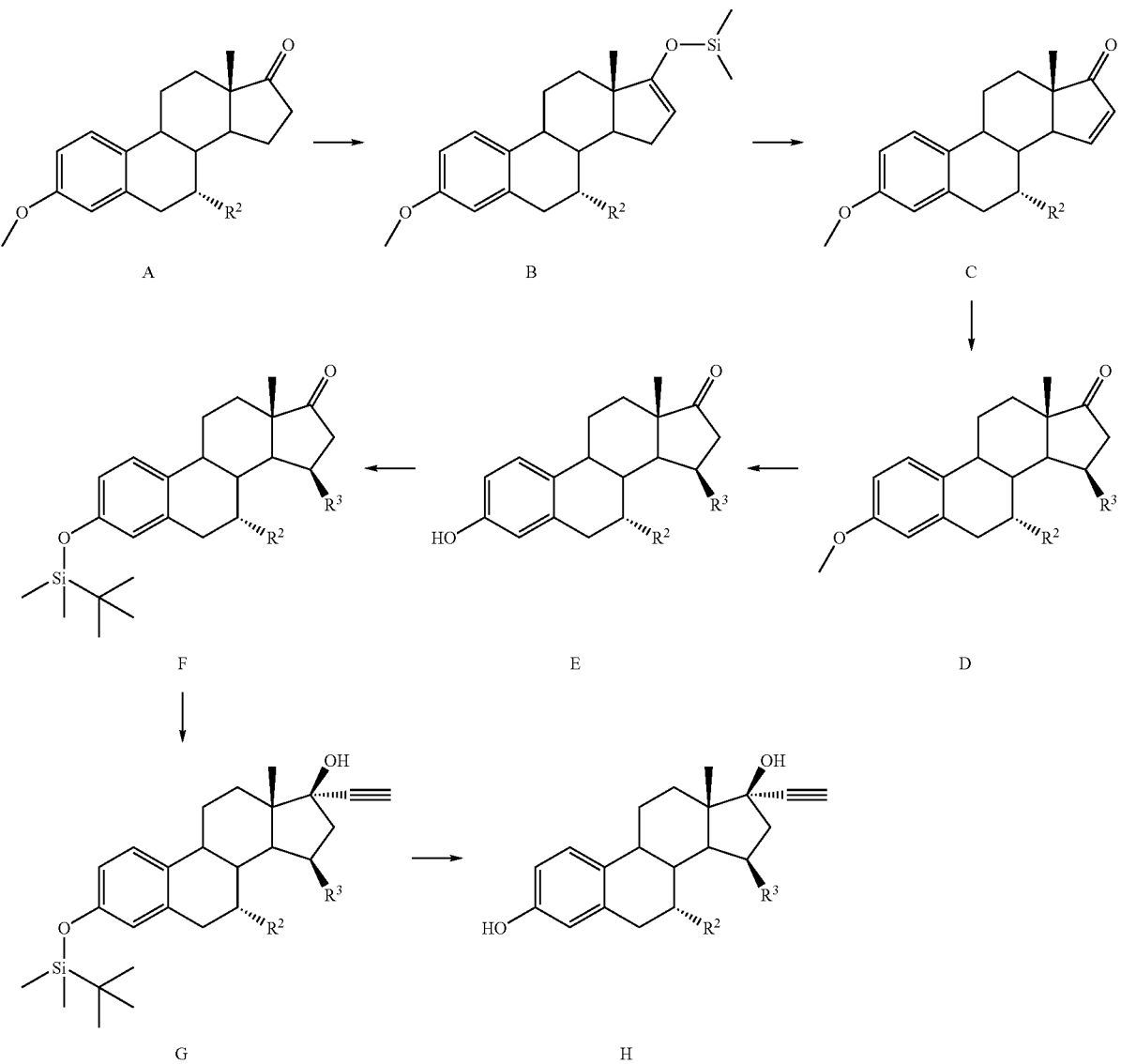

Scheme I by removal of the silyl ether protecting group using e.g., tetrabutyl ammonium fluoride can then provide the desired product H.

(Prodrug) derivatives of the free hydroxy groups of compounds G or H are readily obtained from these compounds by procedures well known in the art, e.g., by acylation using a carboxylic acid chloride in the presence of base or by acylation using a carboxylic acid in the presence of a coupling reagent such as dicyclohexylcarbodiimide etc., followed by removal of the silyl ether protecting group in the case of compounds G.

Compounds of Formula I having the groups as defined in claim 1 and wherein $R^1$ and $R^4$ are hydrogen, were found to have a consistently better selectivity for the estrogen receptor α-subtype combined with a high estrogen α-receptor potency, i.e. with a potency equal to or higher than 1.0% (relative to 17β-estradiol which has an $EC_{50}$ of approximately $4\times10^{-11}$ M and, by definition, a potency of 100%). Such a compound is an agonist at the estrogen α-receptor and is at least 10-fold less active at the estrogen β-receptor and/or is a partial agonist at the estrogen β-receptor, with an efficacy equal to or less than 60% of the maximal activation as induced by 17β-estradiol. This results in high functional selectivity for the estrogen α-receptor, i.e. selectively activating the estrogen α-receptor whilst not or only partially activating the estrogen β-receptor.

The steroids of Formula I wherein $R^1$ and/or $R^4$ are/is not hydrogen are prodrugs, which do not necessarily meet the above definitions. These prodrugs are converted by metabolic processes within the body into compounds wherein $R^1$ and $R^4$ are hydrogen, which compounds do meet said definitions.

Furthermore, the selective (estrogenic) ligands of the present invention surprisingly do not induce a high degree of endometrial proliferation (follicular phase-like changes) and can therefore be used as a medicament for (long-term) treatment and/or prevention of per- and/or post-menopausal (climacteric) complaints and osteoporosis without addition of a progestagenic compound.

The selective estrogen receptor activation profile of the compounds of the present invention makes them suitable for application in therapy.

The present invention further relates to the use of a compound according to Formula I for the manufacture of a medicament for the treatment or prevention of estrogen receptor-related diseases or regulation or treatment or prevention of other estrogen receptor-related physiological conditions.

In a further aspect, the invention relates to the use of a compound of Formula I for the manufacture of a medicament for hormone replacement therapy or hormone treatment. Such use is particularly suitable in women for the indications of peri- and/or post-menopausal (climacteric) complaints and osteoporosis.

In a further aspect, the invention relates to the use of a compound of Formula I for the manufacture of a medicament for use in contraception. For this purpose a compound according to the invention may be administered as part of a treatment regime involving also administration of an appropriate amount of a progestagen. Such regimes are well known in the field of contraception.

Administration of a compound according to the invention will be greatly aided by the manufacture of suitable dosage forms. The present invention therefore also relates to a pharmaceutical composition or dosage form comprising a compound according to the present invention mixed with (a) pharmaceutically acceptable excipient(s), such as the ones described in Gennaro et. al., Remmington: *The Science and Practice of Pharmacy*, $20^{th}$ Edition, Lippincott, Williams and Wilkins, 2000; see especially part 5: pharmaceutical manufacturing. Suitable excipients are described e.g., in the Handbook of Pharmaceutical Excipients, $2^{nd}$ Edition; Editors A. Wade and P. J. Weller, American Pharmaceutical Association, Washington, The Pharmaceutical Press, London, 1994. The mixtures of a compound according to the present invention and (a) pharmaceutically acceptable excipient(s) may be compressed into solid dosage units, such as tablets, or be processed into capsules or suppositories. By means of pharmaceutically suitable liquids the compounds can also be applied as an injection preparation in the form of a solution, suspension, emulsion, or as a spray, e.g., a nasal or buccal spray. For making dosage units e.g., tablets, the use of conventional additives such as fillers, colorants, polymeric binders and the like is contemplated. In general, any pharmaceutically acceptable additive can be used. The compounds of the invention may also be included in an implant, a vaginal ring, a patch, a gel or any other preparation for immediate and/or sustained release.

Suitable fillers with which the pharmaceutical compositions can be prepared and administered include lactose, starch, cellulose and derivatives thereof, and the like, or mixtures thereof used in suitable amounts.

The dosage amounts of the present invention will be in the normal order for estrogenic compounds, e.g., in the order of 0.01 to 100 mg, more in particular 0.1 to 10 m g per administration.

The present invention is illustrated in the following examples:

Scheme II

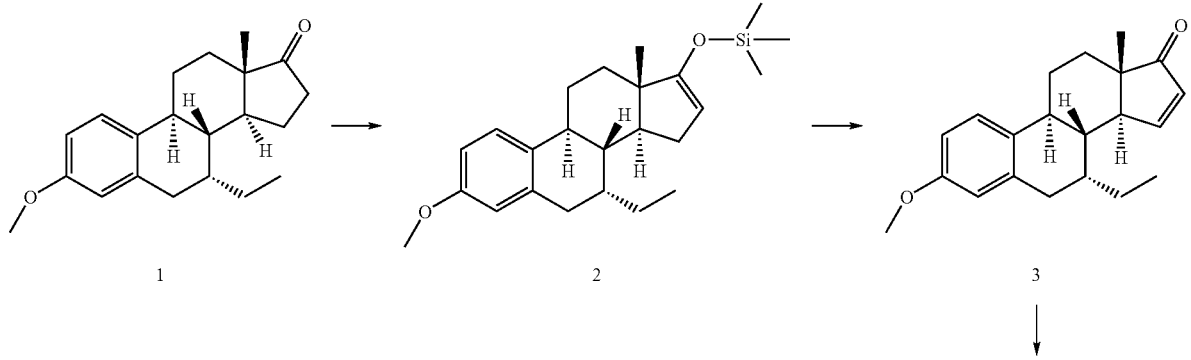

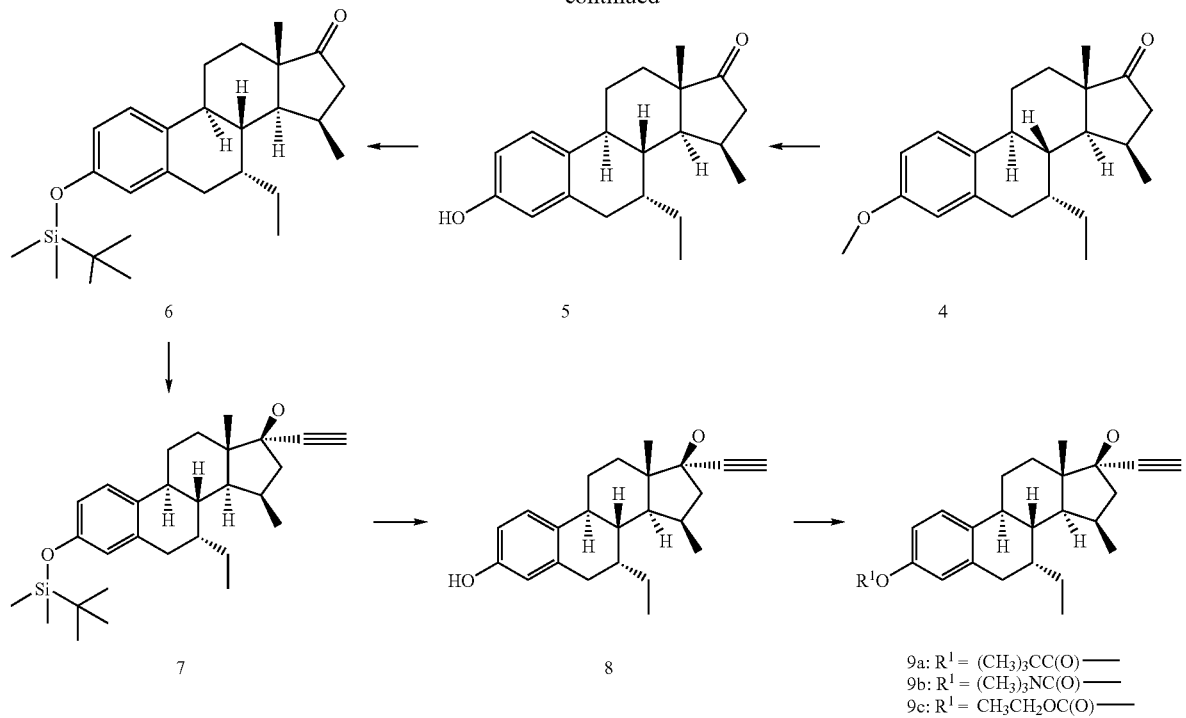

9a: R¹ = (CH₃)₃CC(O)—
9b: R¹ = (CH₃)₃NC(O)—
9c: R¹ = CH₃CH₂OC(O)—

EXAMPLE 1

Preparation of 7α-ethyl-15-β-methyl-19-nor-17α-pregna-1,3,5(10)-trien-20-yne-3,17β-diol (8) (see Scheme II)

Preparation of 7α-ethyl-3-methoxy-estra-1,3,5(10), 15-tetraen-17-one (3)

7α-Ethyl-3-methoxyestrone 1 was prepared from 17β-17-(acetyloxy)-estra-4,6-dien-3-one and ethylmagnesium bromide in analogy with the method described in EP 0869132 A1 (see Example I and Scheme I, Compounds 1-5).

A solution of 7α-ethyl-3-methoxyestrone 1 (1 g) in THF (3 ml) was added dropwise at −60° C. to a solution of LDA [prepared by addition of a 1.6 M solution of n-BuLi in heptane (4.7 ml) at −50° C. to diisopropylamine (2.1 ml) in THF (15 ml)]. The mixture was stirred for ½ h at −60° C. and then treated with trimethylsilyl chloride (2 ml). The reaction mixture was warmed to 0° C. in a period of ½ hr and then poured into a 10% aq. NH₄Cl solution (100 ml) and extracted with ethyl acetate. Washing, drying (Na₂SO₄) followed by concentration provided crude silylenolate 2 (1.1 g) which was used in the next stage without further purification.

To a solution of crude silylenolether 2, (1.1 g) in acetonitrile (15 ml) was added Pd(OAc)₂ (750 mg). The mixture was heated at reflux for 15 minutes. Then water and ethyl acetate were added, the organic mixture was filtered through Celite and the product extracted into ethyl acetate. The organic material thus isolated was purified by passing it through a short silica column, eluting with heptane/ethyl acetate, to give compound 3 (710 mg) as a colourless oil. $R_f$(1) 0.47, $R_f$(2) 0.80, $R_f$(3) 0.46, eluent heptane/ethyl acetate 8/2. NMR (CDCl₃), δ 7.58 (1H), 7.21 (1H), 6.74 (1H), 6.66 (1H), 3.79 (3H, CH₃O), 1.11 (s, 3H, 18-CH₃), 1.00 (t, 3H, ethyl).

Preparation of 7α-ethyl-15β-methyl-3-methoxy-estra-1,3,5(10)-trien-17-one (4)

To a solution of 3, (300 mg) in dry THF (5 ml) was added anhydrous Cu(OAc)₂ (100 mg). The mixture was stirred for 2 min at −70° C., followed by dropwise addition of methylmagnesium chloride (1M in THF, 5 ml). The reaction was warmed in ½ hr to 0° C. and quenched by the addition of 10% aq. NH₄Cl solution. The product was extracted with ethyl acetate and then purified by chromatography over silica gel, using heptane/ethyl acetate as elutant to provide 4 as a white solid (280 mg), m.p. 120-122° C.; NMR (CDCl₃) δ 7.22 (1H), 6.73 (1H), 6.65 (1H), 3.79 (1H), 1.20 (3H, s, 18CH₃), 0.98, 0.96 (6H, 2t, 7α and 15β ethyl).

Preparation of 7α-ethyl-15β-methyl-3-[(trimethylsilyl)oxy]-estra-1,3,5(10)-trien-17-one (6)

To a solution of 4 (270 mg) in dichloromethane (1 ml) was added BF₃.DMS complex (800 μl). The mixture was stirred for 1.5 h and then poured into ice-water and extracted with ethyl acetate. The residue thus obtained was triturated with ether/heptane (1/1) to provide 5, (250 mg) as a light rose amorphous solid; $R_f$ 0.27 (heptane/ethyl acetate 8/2). The material was dissolved in DMF (3 ml), imidazole (300 mg) was added followed by t-butyldimethylsilyl chloride. After stirring for 2 h at room temperature the silylation was completed. The reaction was quenched by addition of ice water, followed by extraction of the product with ethyl acetate. Chromatographic purification over a short silica column (heptane/ethyl acetate 9/1) gave 6 (220 mg) as a stiff colourless oil; $R_f$ 0.60 (heptane/ethyl acetate 8/2). NMR (CDCl₃) δ 7.12 (1H), 6.62 (1H), 6.18 (1H), 1.03 (s, 3H, 18-CH₃), 0.98 (s, 9H, tert.butylsilyl), 0.97, 0.95 (2t, 6H, 7α and 15β ethyl), 0.20 (s, 6H, CH₃-silylether).

Preparation of 7α-ethyl-15β-methyl-19-nor-17α-pregna-1,3,5(10)-trien-20-yne-3,17β-diol (8)

A solution of Li-acetylide was generated by dropwise addition of n-butyllithium (1.6 M in hexane, 5 ml) to 1,2-dibromoethene (300 μl) in dry THF (6 ml) at −60° C. After stirring for 20 minutes, a solution of 6 (220 mg) in THF (2 ml) was added, the cooling device was removed and the reaction was stirred for 1 hr at 0° C. Then 5% $NH_4Cl$ (50 ml) was added, followed by extraction with ethyl acetate. Upon passing of the crude product through a short silica column (eluting with heptane/ethyl acetate 8/2) compound 7 (180 mg) was obtained as a white foam in essentially pure form; $R_f$ 0.28 (heptane/ethyl acetate 8/2), $R_f$ starting material, 0.48. NMR ($CDCl_3$) δ 7.14 (1H), 6.62 (1H), 6.57 (1H, 2.60, acetylene), 0.99 (s, 12H, 18-$CH_3$ and tert.butylsilyl), 0.95 and 0.86 (2×t, 3H, ethyl), 0.20 (s, 6H, dimethylsilyl).

To a solution of 7 (180 mg) in THF (1 ml) was added TBAF (1M in THF, 0.7 ml). The mixture was stirred for 15 mins and then poured onto 10% aq $NH_4Cl$ (20 ml). The product was extracted with ethyl acetate and passed through a short silica column, using heptane/ethyl acetate 7/3 as eluant to give 8 (120 mg) as amorphous material.

NMR (DMSO D6) δ 8.89 (s, phenolic OH), 7.08 (1H), 6.5 (1H), 6.43 (1H), 5.34 (s, 1H, 17-OH), 0.84 (s, 3H, 18-$CH_3$), 0.80 and 0.90 (2×t, 6H, 15β and 7α-ethyl).

EXAMPLE 2

Preparation of 3-pivaloyloxy-7α-ethyl-15β-methyl-19-nor-17α-pregna-1,3,5(10)-trien-20-yne-17β-ol (9a)

Compound 8 (300 mg) was dissolved in pyridine (10 ml). Pivaloyl chloride (1.5 eq.) was added dropwise. After 2 hours the reaction mixture was quenched with water. The reaction mixture was concentrated, redissolved in ethyl acetate, and extracted with aq. sodium bicarbonate and water. The organic layer was dried ($Na_2SO_4$) and concentrated. The residue was purified by chromatography on silica gel (heptane-ethyl acetate (1:0->4:1) to give pure 9a (347 mg). NMR ($CDCl_3$) δ 1.35 (s, 9H, pivaloyl), 1.08 (d, 3H, 155-Me), 1.02 (s, 3H, 18-Me), 0.94 (t, 3H, 7-ethyl). Compounds 9b (289 mg; NMR ($CDCl_3$) δ 3.0 and 3.08 (2×s, 6H, $NMe_2$) 1.08 (d, 3H, 15β-Me), 1.02 (s, 3H, 18-Me), 0.93 (t, 3H, 7-ethyl)) and 9c (283 mg; NMR ($CDCl_3$) δ 4.32 (q, 2H, $OCH_2CH_3$), 1.38 (d, 3H, $OCH_2CH_3$), 1.08 (d, 3H, 15β-Me), 1.02 (s, 3H, 18-Me), 0.93 (t, 3H, 7-ethyl)) were prepared in a similar fashion, but using N,N-dimethylcarbamoyl chloride and ethyloxycarbonyl chloride, respectively.

EXAMPLE 3

The agonistic activity of compounds on the estrogen receptors was determined in an in vitro bioassay with recombinant Chinese hamster ovary (CHO) cells stably co-transfected with the human estrogen receptor α (hERα) or β (hERβ), the rat oxytocin promoter (RO) and the luciferase reporter gene (LUC). The potency of a test compound to stimulate the transactivation of the enzyme luciferase mediated via the estrogen receptors hERα or hERβ, i.e. estrogenic agonistic transactivation, is expressed as percentage (%) relative to the $EC_{50}$ of the standard estrogen 17β-estradiol (potency test compound=($EC_{50}$ 17β-estradiol/$EC_{50}$ test compound)× 100%). The efficacy, i.e. the amount of maximal activation of the receptor by a compound, is expressed as percentage (%) relative to the maximal activation as induced by the standard estrogen 17β-estradiol (efficacy test compound=(maximal activation test compound/maximal activation 17β-estradiol)× 100%). A more detailed description of the methodology can be found in De Gooyer M. E., Deckers G. H., Schoonen W. G. E. J., Verheul H. A. M. and Kloosterboer H. J., *Steroids*, Vol. 68, 2003, pp. 21-30.

ERα/ERβ selectivity is defined as the ratio ERα-potency/ERβ-potency. Compounds of the invention are agonistic at the estrogen α-receptor, with a potency equal to or higher than 1.0% (relative to 17β-estradiol) and are at least 10-fold less active at the estrogen β-receptor (ERα/ERβ selectivity is equal to or higher than 10) and/or are partial agonists at the estrogen β-receptor, with an efficacy equal to or less than 60% of the maximal activation as induced by 17β-estradiol.

Histopathological evaluation of Cynomolgus monkey uterine tissue was performed by a pathologist after an 8 week oral treatment with the test compound in four animals per treatment group. Comparative Compound X was dosed once daily at 40 μg/kg, Comparative Compound Y at 200 μg/kg and Compound 8 at 40 and 200 μg/kg. The following morphological characteristics were examined in H&E stained sections, based on the uterine phases of the normal menstrual cycle in Cynomolgus monkeys.

A. Follicular phase-like changes:
  loose endometrial stroma
  straight endometrial glands
  hypertrophy of endometrial epithelium
  mitotic figures
  hypertrophy of myometrium
  early angiogenesis (sprouting or early proliferation)
  basal secretion
B. Luteal phase-like changes
  pseudodecidually enlarged stromal cells
  coiling of endometrial glands
  late angiogenesis (spiral artery formation)
  vacuolation of endometrial epithelium
  luminal secretion
C. Ovariectomized or non-stimulated (atrophic) endometrium
  compact endometrial stroma
  atrophy of endometrial epithelium
  atrophy of endometrial glands
  atrophy of myometrium The severity of each of these above-mentioned findings was scored using a scale of grading:
  grade 0: finding not present
  grade 1: minimal, very few, very small
  grade 2: slight, few, small
  grade 3: moderate, moderate number, moderate size
  grade 4: marked, many, large
  grade 5: massive, extensive number, extensive size For each animal this grading was done. Then the average score per treatment group was calculated for each characteristic. Finally, an average score per category, atrophic, follicular- or luteal phase-like, was calculated from the average individual characteristics. A favourable endometrial safety profile for a compound is characterized by less compound-induced follicular phase-like activity combined with more luteal phase-like characteristics and/or atrophic endometrium.

The data for Compound 8 and for the Comparative Compounds X (17α-ethynyl-17β-estradiol, Formula I wherein $R^1$-$R^4$ are all H) and Y (17β-estradiol) are presented in Table 1 (in vitro cellular data) and Table 2 (in vivo data).

TABLE 1

| Compound | ERα-potency (%) | ERβ-potency (%) | ERβ-efficacy (%) | ERα/ERβ-selectivity (potency) |
|---|---|---|---|---|
| 8 | 23.45 | 1.54 | 40 | 15.2 |
| X | 102.8 | 20.70 | 104 | 5.0 |
| Y | 100.0 | 100.0 | 100 | 1.0 |

The results shown in Table 1 demonstrate that compounds of the invention have a consistently better functional selectivity for the estrogen receptor α-subtype combined with a high estrogen α-receptor potency, i.e. selectively activating the estrogen α-receptor whilst not or only partially activating the estrogen β-receptor. Compound 8 shows an estrogen α-receptor potency of 23.45% and is 15.2-fold selective for the estrogen α-receptor over the estrogen β-receptor and is a partial agonist at the estrogen β-receptor with an efficacy of 40%. The closely related compounds 17α-ethynyl-17β-estradiol (Compound X) and 17β-estradiol (Compound Y) show equal preference for both estrogen receptor subtypes and are full agonists at the estrogen β-receptor.

TABLE 2

| | Monkey Endometrial profile (scores) | | |
|---|---|---|---|
| Compound | Follicular | Luteal | Atrophic |
| 8: 40 μg/kg | 0.0 | 0.0 | 3.0 |
| 8: 200 μg/kg | 0.5 | 0.2 | 2.3 |
| X: 40 μg/kg | 2.8 | 0.4 | 0 |
| Y: 200 μg/kg | 3.6 | 0.2 | 0 |

The favourable endometrial safety profile of compounds of the invention is surprising since the closely related compounds 17α-ethynyl-17β-estradiol and 17β-estradiol both stimulate the endometrium as is demonstrated in Table 2 by clear signs of follicular phase-like activity with only marginal luteal phase-like activity and therefore no atrophic endometrium.

EXAMPLE 4

Rat female sexual behavior is hormone dependent. In estrogen-primed female rats progesterone clearly enhances female sexual or lordosis behavior. However, progesterone is not effective in inducing lordosis in ovariectomised females that have not received estrogen (see also J. B. Becker, S. M. Breedlove and D. Crews (Eds.), Behavioral Endocrinology, 1992, pp. 82-84).

The capacity of test compounds to facilitate progesterone-induced lordosis behavior in female ovariectomised rats was used to demonstrate in vivo estrogenic activity upon oral dosing of such compounds. Females were pre-treated for three days with test compound followed by treatment with a progestagen on the fourth day. Four hours after progesterone treatment sexual behavior of the female rat was measured in the presence of a male rat by counting the number of lordosis responses during 10 minutes.

Prodrugs of Compound 8, wherein $R^1$ is pivaloyl (Compound 9a), $R^1$ is dimethyl-carbamoyl (Compound 9b) or $R^1$ is ethoxycarbonyl (Compound 9c) all demonstrated to be active estrogenic compounds upon oral dosing at 1 mg/kg.day.

The invention claimed is:

1. A 15β-substituted steroidal compound of Formula I:

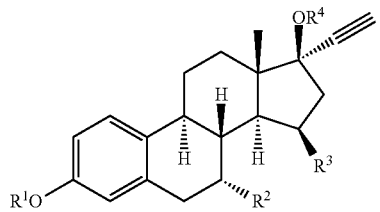

wherein $R^1$ is H, $C_{1-5}$ alkyl, $C_{1-12}$ acyl, di-($C_{1-5}$ alkyl)aminocarbonyl, ($C_{1-5}$ alkyl)oxycarbonyl or sulfamoyl;
$R^2$ is $C_{1-3}$ alkyl, $C_{2-3}$ alkenyl or $C_{2-3}$ alkynyl, each of which may be optionally substituted with a halogen;
$R^3$ is $C_{1-2}$ alkyl, ethenyl or ethynyl, each of which may be optionally substituted with a halogen; and
$R^4$ is H or $C_{1-12}$ acyl.

2. The compound according to claim 1, wherein $R^1$ and $R^4$ are both H.

3. The compound according to claim 1, wherein the compound is 7α-ethyl-15β-methyl-19-nor-17α-pregna-1,3,5(10)-trien-20-yne-3,17β-diol.

4. A pharmaceutical composition comprising a compound according to claim 1 and a pharmaceutically acceptable excipient.

5. A pharmaceutical composition comprising a compound according to claim 2 and a pharmaceutically acceptable excipient.

6. A pharmaceutical composition comprising the compound of claim 3 and a pharmaceutical acceptable excipient.

7. A method for the treatment of a disease or condition selected from the group consisting of osteoporosis and climacteric complaints, wherein the climacteric complaints are selected from the group consisting of hot flushes, sweating and mood swings, the method comprising: administering to a human an effective amount of the compound according to claim 1.

8. The method according to claim 7, wherein the disease or condition is climacteric complaints.

9. The method according to claim 7, wherein the disease or condition is osteoporosis.

10. A method of contraception comprising: administering to a woman an effective amount of the compound according to claim 1.

11. A method of treating osteoporosis in a human comprising: administering to the human an effective amount of the compound according to claim 3.

12. A method of treating climacteric complaints selected from the group consisting of hot flushes, sweating and mood swings in a human comprising: administering to the human an effective amount of the compound according to claim 3.

13. A method of contraception comprising: administering to a woman an effective amount of the compound according to claim 3.

* * * * *

UNITED STATES PATENT AND TRADEMARK OFFICE
CERTIFICATE OF CORRECTION

| | | |
|---|---|---|
| PATENT NO. | : 7,838,516 B2 | Page 1 of 1 |
| APPLICATION NO. | : 11/662166 | |
| DATED | : November 23, 2010 | |
| INVENTOR(S) | : Loozen et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 360 days.

Signed and Sealed this

Fourth Day of October, 2011

David J. Kappos
*Director of the United States Patent and Trademark Office*